(12) United States Patent
Guit et al.

(10) Patent No.: US 6,333,412 B1
(45) Date of Patent: Dec. 25, 2001

(54) PROCESS FOR THE PREPARATION OF ε-CAPROLACTAM

(75) Inventors: Rudolf P. M. Guit, Maastricht (NL); Samuel L. Lane, Beaumont, TX (US)

(73) Assignees: DSM N.V., Heerlen (NL); E.I. Dupont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/635,717

(22) Filed: Aug. 9, 2000

Related U.S. Application Data

(63) Continuation of application No. PCT/NL99/00080, filed on Feb. 16, 1999.

(30) Foreign Application Priority Data

Feb. 18, 1998 (EP) .................................................. 98200520

(51) Int. Cl.⁷ ................................................. C07D 201/08
(52) U.S. Cl. .......................................................... 540/538
(58) Field of Search .............................................. 540/538

(56) References Cited

U.S. PATENT DOCUMENTS

| | | | |
|---|---|---|---|
| 4,731,445 | 3/1988 | Hutmacher et al. ................. | 540/538 |
| 4,767,857 | 8/1988 | Merger et al. ........................ | 540/538 |
| 5,700,934 | 12/1997 | Wolters et al. ....................... | 540/538 |
| 5,717,089 | 2/1998 | Wolters et al. ....................... | 540/538 |
| 5,977,356 | * 11/1999 | Chu et al. ............................. | 540/538 |

FOREIGN PATENT DOCUMENTS

WO 9 730974   8/1997   (WO) .

* cited by examiner

*Primary Examiner*—Bruck Kifle
(74) *Attorney, Agent, or Firm*—Pillsbury Winthrop LLP

(57) ABSTRACT

Process to prepare ε-caprolactam starting from a starting mixture containing a 6-aminocaproate ester, in which in a first step (1) the 6-aminocaproate ester is converted into 6-aminocaproic acid and 6-aminocaproamide by reaction with water in the presence of ammonia at a temperature of between 50 and 250° C., with a separate or simultaneous removal of alcohol(s), and in a subsequent step (2) the 6-aminocaproic acid and 6-aminocaproamide are cyclizised at an elevated temperature, wherein in step (1) the 6-aminocaproate ester is converted into 6-aminocaproic acid and 6-aminocaproamide in the presence of an amount higher than 2 wt. % and less than or equal to 25 wt. % $NH_3$ (relative to the total amount of organic compounds, water and ammonia present in step (1)).

8 Claims, No Drawings

PROCESS FOR THE PREPARATION OF ε-CAPROLACTAM

This is a Continuation of International Appln. No. PCT/NL99/00080 filed Feb. 16, 1999 which designated the U.S.

The invention relates to a process to prepare ε-caprolactam from a starting mixture containing a 6-aminocaproate ester, in which in a first step (1) the 6-aminocaproate ester is converted into 6-aminocaproic acid and 6-aminocaproamide by reaction with water in the presence of ammonia at a temperature of between 50 and 250° C., with a separate or simultaneous removal of alcohol(s), and in a subsequent step (2) the 6-aminocaproic acid and 6-aminocaproamide are cyclizised at an elevated temperature.

Such a process is described in U.S. Pat. No. 4,731,445. This publication describes a process in which first methyl 5-formylvalerate is contacted with ammonia and hydrogen in the presence of methanol as solvent and a hydrogenation catalyst. In this step methyl 6-aminocaproate and a small amount of ε-caprolactam is obtained. In a second step, the excess ammonia and hydrogen are removed from the reaction mixture. In a third step, the methyl 6-aminocaproate is reacted with water in the presence of a small amount (0.1 to 2 wt. %) of ammonia at a temperature of 50 to 250 ° C. The released methanol is simultaneously removed. Example 1 of U.S. Pat. No. 4,731,445 discloses the reaction of methyl 6-aminocaproate with water in the presence of an almost negligible amount of ammonia at a temperature of about 100° C. The resulting aqueous mixture, which mixture contains 6-aminocaproic acid and small amounts of 6-minocaproamide and ε-caprolactam, is heated to a emperature of 330° C. In this step the 6-aminocaproic acid and 6-aminocaproamide reacts by cyclization to ε-caprolactam.

A disadvantage of the process described in U.S. Pat. No. 4,731,445 is that the rate of the reaction in the third step in which 6-aminocaproate ester is converted into 6-aminocaproic acid and 6-aminocaproamide is relatively small. Furthermore it would be advantageous if the reaction rate of 6-aminocaproate ester into 6-aminocaproic acid and 6-aminocaproamide could be improved in order to make this process more attractive for commercial use on a large scale.

The object of the invention is to provide a process according to which the 6-aminocaproate ester can be converted into 6-aminocaproic acid and 6-aminocaproamide with an improved reaction rate.

This object is achieved in that in step (1) the 6-aminocaproate ester is converted into 6-aminocaproic acid and 6-aminocaproamide in the presence of an amount higher than 2 wt. % and less than or equal to 25 wt. % $NH_3$ (relative to the total amount of the starting mixture).

It has been found that with the process of the invention the rate of the reaction of 6-aminocaproate ester into 6-aminocaproic acid and 6-aminocaproamide in step (1) is higher than the rate of the reaction disclosed in U.S. Pat. No. 4,731,445. An advantage of the process according to the invention is that a smaller volume of process equipment can be used in step (1) for obtaining comparable degrees of conversion of 6-aminocaproate ester to 6-aminocaproic acid and 6-aminocaproamide. From an economical/investment point of view smaller process equipment is desired.

In the first step (1) of the process according to the invention 6-aminocaproate ester is converted into 6-aminocaproic acid and 6-aminocaproamide by reaction with water in the presence of ammonia.

The starting mixture fed to the first step therefore should at least contain 6-amino caproate ester, water and ammonia. Other compounds may be present in the starting mixture, e.g. methanol.

The amount of 6-aminocaproate ester in the liquid mixture fed to the first step (1) (starting mixture) generally exceeds 0.5 wt. % calculated on the amount of organic compounds present in the starting mixture. Organic compounds are here defined as ε-caprolactam and ε-caprolactam precursors and side-reaction products, which may be present in small amounts. ε-Caprolactam precursors are defined as 6-aminocaproic acid, 6-aminocaproate ester, 6-aminocaproamide and oligomers of these compounds.

In the process according to the invention 6-aminocaproic acid and/or 6-aminocaproamide may also be present in the starting mixture. Next to the 6-aminocaproate ester and optionally the 6-aminocaproic acid and/or 6-aminocaproamide, also ε-caprolactam and/or oligomers of 6-aminocaproic acid and/or 6-aminocaproamide may be present. A typical composition of organic compounds which can be used in the starting mixture for the present invention comprises between 0.5 and 100 wt. % 6-aminocaproate ester, 0 and 30 wt. % 6-aminocaproic acid, 0 and 50 wt. % 6-aminocaproamide, 0 and 50 wt. % ε-caprolactam and between 0 and 30 wt. % of the earlier mentioned oligomers in which the total of these fractions is about 100 wt. % of the organic compounds.

Ammonia and/or water may be added to or removed from and/or may already be present in a reaction mixture which also contains 6-aminocaproate ester. Thus the ammonia and/or water concentration can be kept and/or adjusted to the desired value within the general and preferred ranges before feeding the starting mixture to the first step (1) of the process according to the invention. Removal of ammonia and/or water can be done by for example flashing or stripping.

The amount of ammonia present in the starting mixture is higher than 2 and less than or equal to 25 wt. %. The term "ammonia" means free $NH_3$ and does not include the amount of $NH_3$ present in the form of for example a terminal amide group of a compound optionally present in the starting mixture. An example of such a compound is 6-aminocaproamide. The ammonia concentration in step (1) is preferably lower than 20 wt. %, more preferably lower than 15 wt. %. The ammonia concentration in step (1) is preferably higher than 3 wt. % and more preferably higher than 5 wt. %.

The total concentration of organic compounds essentially consisting of 6-aminocaproate ester and—if present—6-aminocaproic acid, 6-aminocaproamide, ε-caprolactam and oligomers of 6-aminocaproic acid and 6-aminocaproamide in the starting mixture is preferably between about 0.2 and 50 wt. %. The sum of the amounts of organic compounds, ammonia, water and other compounds like methanol in the starting mixture is 100 wt. %.

The 6-aminocaproate ester compound can be represented by the following general formula:

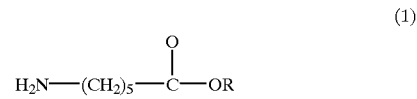

(1)

where R is preferably an organic group with 1 to 20 carbon atoms and more preferably with 1 to 6 carbon atoms. The organic group is an alkyl, cycloalkyl, aryl or aralkyl group. More preferably R is an alkyl group. Examples of R groups include methyl, ethyl, propyl, isopropyl, n-butyl, tert-butyl, isobutyl, cyclohexyl, benzyl and phenyl. By preference R is methyl or ethyl.

The temperature in step (1) of the process according to the invention is between 50 and 250° C., preferably between 60 and 160° C. and most preferably between 90 and 140° C.

The pressure of the first step (1) is not critical. Depending on the pressure the reactor can be operated as a full liquid mixture or as a mixture where a liquid and a vapor phase coexist. Methanol and ammonia may be partly stripped from the mixture.

The starting mixture of the process according to the invention may be obtained with various known processes. For this invention it is not critical how the starting mixture is obtained.

The starting mixture may be, for example, obtained as the reaction product of the reduction of 5-cyanovalerate ester.

The starting mixture of the process according to the invention may also for example be obtained as the reaction product of the reductive amination of a 5-formylvalereate ester. Examples of possible processes are described in EP-A-729943, EP-A-729944, U.S. Pat. Nos. 4,766,237, 4,730,041, 4,731,445 and 5,068,398.

The reductive amination mixture may contain, next to the 6-aminocaproate ester and optionally 6-aminocaproic acid, 6-aminocaproamide, ε-caprolactam and/or oligomers, some alcohol. The alcohol generally is the corresponding alcohol of the ester group of the 6-aminocaproate ester. The alcohol can be separated from the reductive amination mixture by means of stripping or distillation before this mixture is fed to the first step (1) of the process according to the invention.

The process according to the invention can be applied with particular advantage using an aqueous mixture obtained in a previous process step, which mixture already contains 6-aminocaproate ester and optionally 6-aminocaproic acid, 6-aminocaproamide, ε-caprolactam and/or oligomers. The aqueous mixture containing the 6-aminocaproate ester, 6-aminocaproic acid, 6-aminocaproamide, ε-caprolactam and/or oligomers can for example be obtained by a process as described in EP-A-729944.

In a step simultaneous with or subsequent to the first step (1), the alcohol(s) is (are) separated from the mixture obtained in step (1) before feeding this mixture to the cyclisation step (2). This alcohol(s) is (are) formed in the first step (1) of the process according to the invention. The alcohol(s) can also already be present in the starting mixture of the process according to the invention, which mixture is obtained in a previous step, for example reductive amination, in which the alcohol is used as solvent and/or formed.

From WO-A-9730793 it is known that the amount of alcohols in the mixture which is fed to the cyclisation section should be lower than 1 wt. %, more preferably lower than 0.1 wt. %. This is because the presence of alcohol during the cyclization promotes the formation of the corresponding N-substituted caprolactam, an undesired by-product. The formation of these N-substituted caprolactam by-products has a negative influence on ε-caprolactam yield. Furthermore, it is not easy to remove these N-substituted caprolactam by-products (especially N-methyl and N-ethyl caprolactam) from ε-caprolactam.

The alcohol to be separated is generally a $C_1$–$C_6$ alkanol such as, for example, methanol, ethanol, propanol, butanol, pentanol or hexanol, or as an aromatic alcohol, for example, phenol. When 6-aminocaproic ester is obtained starting from a 5-formylvalerate ester or 5-cyanovalerate ester, the alcohol is generally the alcohol which corresponds with the ester group of these esters. Generally, these corresponding alcohols are methanol or ethanol.

Separation of the alcohol may be performed by any known method known to the man skilled in the art, for example, distillation or stripping. An example of separating the alcohol by means of distillation is described in U.S. Pat. No. 4,731,445. Preferably, the alcohol is removed by stripping the aqueous mixture with steam as described in WO-A-9730973.

The first step (1) of the process according to the invention can be performed batch wise or continuously. In a commercial process the reaction is preferably carried out in a continuous mode in a suitable reactor. Examples of suitable reactors are plug flow reactors, a continuously stirred tank reactor or several stirred reactors in series. Reactors with plug flow characteristic are preferred because high conversion degrees of the 6-aminocaproate esters can be obtained.

The aqueous mixture obtained in step (1), containing 6-aminocaproic acid and 6-aminocaproamide and optionally some non-converted 6-aminocaproate ester, ε-caprolactam and oligomers is subsequently fed to the cyclisation step (2) of the process according to the invention. It has been found that not only the presence of alcohols during the cyclisation, but also the presence of 6-aminocaproate ester, promotes the formation of undesired N-substituted ε-caprolactam. It is therefore advantageous to cyclizise the ε-caprolactam precursors to ε-caprolactam in the presence of amounts of alcohol and 6-aminocaproate ester as low as possible.

Preferably, the following steps are performed continuously in the process according to the invention:

a) reacting the 6-aminocaproate ester with water in the presence of 2 to 25 wt. % ammonia, b) separating the alcohol from the aqueous mixture;

c) feeding the resulting aqueous mixture to a reaction zone in which the cyclization is performed; and d) separating ε-caprolactam from the mixture leaving the cyclization zone.

The cyclization step (2) of the process according to the invention can be performed in any known manner, e.g. in the liquid or in the gas phase. Examples of possible liquid phase processes are described in U.S. Pat. No. 4,730,040 and EP-A-729944. Examples of possible gas phase processes are described in U.S. Pat. Nos. 4,599,199 and 3,658,810.

In a gas phase cyclisation process, the mixture, preferably concentrated, as obtained after having separated the alcohols from the aqueous mixture of step (1), is contacted with superheated steam. The gas phase process is performed at a temperature of between 150 and 500° C., preferably at a temperature between 250 and 400° C., more preferably at a temperature of between 270 and 350° C. The gas phase process is performed at a pressure of between atmospheric pressure and 2 MPa, preferably between 0.5 and 2 MPa, more preferably below 1.5 MPa. The gas phase processes are advantageous because ε-caprolactam is obtained in a gaseous steam phase in which no or practically no oligomers are present. A gas phase cyclization is preferably performed as discussed below.

The mixture to be cyclisised is preferably contacted with the superheated steam as a liquid, for example as a melt.

At least a part of the water present in the mixture is preferably removed, for example by distillation at a temperature of 60–160° C., preferably at a temperature of 80–140° C. It has been found that the amount of water in the mixture which is fed to the cyclization section is preferably as low as possible.

Preferably the mixture containing water and organic compound(s) is brought into contact with the steam as a liquid mixture containing between 0–50 wt. % water, more preferably between 0–20 wt. % water. The organic compounds can even be fed to the reactor in a finely divided solid form.

The temperature during the contacting with the superheated steam is between 250 and 400° C. and preferably between 270 and 350° C. The pressure is between 0.5 and 2 MPa. Preferably the pressure is below 1.5 MPa. Temperatures higher than 350° C. are more disadvantageous because of the possible occurence of degradation reactions causing yield loss and causing undesirable by-products making the purification more difficult.

In a continuous process the steam-feed ratio (in weight) is preferably between 1 and 20. This feed is the total weight of 6-aminocaproic acid, 6-aminocaproamide, oligomers and ε-caprolactam present in the mixture. This feed does not include any water which may be present.

The process is preferably performed as a continuous process in which steam is continuously fed to a reaction zone in which the mixture is present. More preferably the mixture is continuously or semi-continuously fed to the reaction zone as an aqueous mixture, in which the feed has a temperature of between room temperature and the temperature of the reactor zone.

The continuously operated process according to the invention can be practiced in a reactor apparatus which is provided with an inlet for the feed mixture, an outlet for the steam/ε-caprolactam product and means for supplying steam such that the steam is contacted with the mixture. The reactor is optionally equiped with a heating device and optionally with a mixing device. To this reactor the feed mixture and the steam can be continuously fed. A possible reactor is a fluidized bed reactor containing inert particles in which the bed is kept fluidized by the steam. Another example of a reactor is a horizontal tube reactor having a rotating axis on which axis means for mixing and/or transport are present. Also means may be present which prevent fouling of the interior vessel wall and which promote an optimal steam/substrate contact area for mass-transfer. Examples of other suitable reactors are packed tower-type reactor, one or multiple staged bubble columns, a gas lift loop reactor or a multi-tube reactor.

The gas phase obtained in the process according to the invention will comprise steam and ε-caprolactam and some ammonia may be present. The ε-caprolactam can be isolated from this gaseous stream obtained by the process according to the invention by normal methods known to one skilled in the art, for example as described in U.S. Pat. No. 3,658,810. Preferably ε-caprolactam is isolated by partial condensation in which a concentrated aqueous phase containing ε-caprolactam and a gaseous phase containing steam is obtained. The steam can be reused in the second step (2) of the process according to the invention, for example by first passing steam via a heat exchanger. ε-caprolactam can be isolated from the condensed aqueous mixture by any separation technique, for example distillation or extraction. The water phase, poor in ε-caprolactam, can be reused in the process.

The cyclization can also be performed in the liquid phase at super atmospheric pressures such as, for example described in U.S. Pat. No. 4,730,040 and EP-A-729944. High yields of ε-caprolactam of high quality can be obtained with a liquid phase cyclization process. Preferably a liquid phase cyclization is performed as discussed below.

The concentration of ammonia in the cyclization is preferably below about 5 wt. % and more preferably below about 3 wt. % and most preferably below about 1 wt. %. High concentrations of ammonia have a negative effect on the yield to ε-caprolactam per pass in a continuous process.

The concentration of ε-caprolactam and ε-caprolactam precursors in the cyclization is preferably between about 5 and about 50 wt. % and more preferably between about 10 and about 35 wt. %.

The elevated temperature of the cyclization is preferably between about 200° C. and about 350° C., and more preferably the temperature is higher than about 290° C. because a higher yield to ε-caprolactam per pass is possible.

The pressure is preferably between about 5.0 and about 20 MPa. Normally this pressure will be greater than or equal to the resulting pressure of the liquid reaction mixture and the temperature employed.

The cyclization can be performed continuously in process equipment resulting in high and low rates of backmixing, such as described in EP-A-729944.

The ε-caprolactam can subsequently be purified by methods known for purifying ε-caprolactam obtained by Beckmann rearrangement. An examplary method of purifying ε-caprolactam is described in U.S. Pat. No. 5,496,941.

The ε-caprolactam can be separated from the reaction mixture obtained in the cyclization by for example crystallization, extraction or by distillation. The ε-caprolactam is preferably separated by extraction. With a process as for example described in WO-A-9730028.

Examples I–IX and Comparative Experiments A–D

An aqueous mixture, containing 20 wt. % methyl-6-aminocaproate, 6.5 wt. % methanol, x wt. % $NH_3$ and 100-(20+6.5+x) wt. % $H_2O$, was fed to a packed-bed plug flow reactor. The bed was 0.35 m long with a diameter of $1.1 \times 10^{-2}$ m, and was packed with 1 mm glass beads. The liquid hold-up time in the reactor was varied from 10–45 minutes in all runs. The reactor was kept at a temperature of y° C. The reactor pressure was 7 MPa. The results are summarized in Table 1. The initial rate constants were determined by measuring the conversion levels obtained between residence time of 10 to 45 min. The table 1 presents the conversion obtained at a residence time of 30 min as a function of the ammonia concentration and measured reaction rate.

TABLE 1

| | x wt. % $NH_3$ | 100 − (20 + 6.5 + x) wt. % $H_2O$ | temperature (y ° C.) | first order reaction rate constant (min$^{-1}$) | conversion of M6AC |
|---|---|---|---|---|---|
| Example | | | | | |
| I | 3.5 | 70 | 100 | 0.092 | 93.6 |
| II | 7 | 66.5 | 100 | 0.10 | 95.0 |
| III | 15 | 68.5 | 100 | 0.099 | 94.8 |
| IV | 30 | 43.5 | 100 | 0.054 | 80.3 |
| V | 3.5 | 70 | 140 | 0.20 | 99.8 |
| VI | 7 | 66.5 | 140 | 0.21 | 99.8 |
| VII | 15 | 58.5 | 140 | 0.18 | 99.6 |
| VIII | 30 | 43.5 | 120 | 0.093 | 93.8 |
| IX | 3.5 | 70 | 120 | 0.13 | 98.1 |
| X | 7 | 66.5 | 120 | 0.15 | 99.0 |
| XI | 15 | 58.5 | 120 | 0.13 | 98.1 |
| Comp. Exp. | | | | | |
| A | 1.5 | 72 | 100 | 0.082 | 91.3 |
| B | 1.5 | 72 | 120 | 0.11 | 96.6 |
| C | 1.5 | 72 | 140 | 0.16 | 99.2 |
| D | 0 | 73.5 | 120 | 0.093 | 93.9 |

What is claimed is:

1. Process to prepare ε-caprolactam from a starting mixture containing a 6-aminocaproate ester in an amount higher than 0.5 wt % calculated on the amount of organic compounds in the starting mixture, in which in a first step (1) the 6-aminocaproate ester is converted into 6-aminocaproic acid and 6-aminocaproamide by reaction with water in the presence of ammonia at a temperature of between 50 and 250° C., with a separate or simultaneous removal of alcohol(s), and in a subsequent step (2) the 6-aminocaproic acid and 6-aminocaproamide are cyclizised at an elevated temperature, characterized in that in step (1) the 6-aminocaproate ester is converted into 6-aminocaproic acid and 6-aminocaproamide in the presence of an amount higher than 3 wt. % and less than or equal to 25 wt. % $NH_3$ (relative to the total amount of organic compounds, water and ammonia present in step (1)).

2. Process according to claim 1, characterized in that the first step (1) is performed in the presence of 5–15 wt. % ammonia.

3. Process according to claims 1, characterized in that the 6-aminocaproate ester is a $C_1$–$C_6$ alkyl 6-aminocaproate ester.

4. Process according to claim 1, characterized in that the temperature in step (1) is between 60 and 160° C.

5. Process according to claim 1, characterized in that the starting mixture comprises a composition of organic compounds with between 0.5 and 100 wt. % 6-aminocaproate ester, 0 and 30 wt. % 6-aminocaproic acid, 0 and 50 wt. % 6-aminocaproamide, 0 and 50 wt. % ε-caprolactam and 0 and 30 wt. % oligomers of 6-aminocaproic acid and 6-aminocaproamide, in which the total of all these fractions count up to 100 wt. % of the organic compounds.

6. Process according to claim 5, characterized in that the amount of 6-aminocaproate ester and, if present, 6-aminocaproic acid, ε-caprolactam and oligomers of 6-aminocaproic acid and 6-aminocaproamide, in the starting mixture is between 0.5 and 50 wt. % of the organic compounds.

7. Process according to claim 1, characterized in that the following steps are performed continuously:

a) reacting the 6-aminocaproate ester with water in the presence of 3 to 25 wt. % ammonia, b) separating the alcohol from the aqueous mixture;

c) feeding the resulting aqueous mixture to a reaction zone in which the cyclization is performed; and d) separating ε-caprolactam from the mixture leaving the cyclization zone.

8. The process of claim 1, wherein the 6-aminocaproate ester is converted into 6-aminocaproic acid and 6-aminocaproamide in step (1) in the presence of an amount of $NH_3$ between 3.5 wt % and 25 wt %, relative to the total amount of organic compounds, water and ammonia present in step (1).

* * * * *